(12) United States Patent
Rader et al.

(10) Patent No.: US 12,029,559 B2
(45) Date of Patent: Jul. 9, 2024

(54) WEARABLE DEVICES FOR MONITORING PHYSIOLOGICAL CHANGES AND METHODS OF USE

(71) Applicant: EFFERENT LABS, INC., Buffalo, NY (US)

(72) Inventors: William K. Rader, Huger, SC (US); Spencer Z. Rosero, Pittsford, NY (US)

( * ) Notice: Subject to any disclaimer, the term of this patent is extended or adjusted under 35 U.S.C. 154(b) by 685 days.

(21) Appl. No.: 16/991,456

(22) Filed: Aug. 12, 2020

(65) Prior Publication Data
US 2021/0045660 A1 Feb. 18, 2021

Related U.S. Application Data

(60) Provisional application No. 62/885,599, filed on Aug. 12, 2019.

(51) Int. Cl.
| | | |
|---|---|---|
| *A61B 5/145* | (2006.01) | |
| *A61B 5/00* | (2006.01) | |
| *A61B 5/01* | (2006.01) | |
| *A61B 5/1459* | (2006.01) | |
| *A61M 5/142* | (2006.01) | |

(52) U.S. Cl.
CPC .......... *A61B 5/1459* (2013.01); *A61B 5/0008* (2013.01); *A61B 5/01* (2013.01); *A61B 5/14514* (2013.01); *A61B 5/14546* (2013.01); *A61B 5/6832* (2013.01); *A61B 2560/0443* (2013.01);
(Continued)

(58) Field of Classification Search
CPC . A61B 5/1459; A61B 5/14514; A61B 5/0008; A61B 5/01; A61B 5/14546; A61B 5/6832; A61B 2560/0443; A61M 5/14248; A61M 5/14276; A61M 2205/505
See application file for complete search history.

(56) References Cited

U.S. PATENT DOCUMENTS

| | | |
|---|---|---|
| 7,208,286 B2 | 4/2007 | Simpson et al. |
| 8,466,286 B2 | 6/2013 | Bellott et al. |
| | (Continued) | |

FOREIGN PATENT DOCUMENTS

| | | | |
|---|---|---|---|
| WO | 00/33065 A1 | 6/2000 | |
| WO | WO-0033065 A1 * | 6/2000 | ......... A61B 5/14532 |

OTHER PUBLICATIONS

PCT International Search Report and Written Opinion dated Oct. 28, 2020, International Application No. PCT/US2020/045892, pp. 1-8.
(Continued)

*Primary Examiner* — Eric J Messersmith
(74) *Attorney, Agent, or Firm* — BioPharma Law Group, PLLC; Joanna T. Brougher, Esq.

(57) ABSTRACT

A wearable device for monitoring physiological changes in a patient is provided. The device can include a housing adapted to being secured to a patient's body, the housing comprising a needle configured for fluid contact with a bodily fluid under a skin surface; a chamber having a cell layer and configured to monitor physiological changes in the bodily fluid and to generate one or more signals associated with the physiological changes; and a reader for detecting and/or decoding signals from the cell layer to monitor physiological changes in the patient. The device is capable of engaging in a two-way communication with a second device through transmission of one or more signals.

13 Claims, 9 Drawing Sheets

(52) U.S. Cl.
CPC ..... *A61M 5/14248* (2013.01); *A61M 5/14276* (2013.01); *A61M 2205/505* (2013.01)

(56) References Cited

U.S. PATENT DOCUMENTS

| | | | |
|---|---|---|---|
| 10,939,488 B2* | 3/2021 | Ng | H04W 76/14 |
| 2003/0108980 A1 | 6/2003 | Sayler et al. | |
| 2003/0135333 A1 | 7/2003 | Aceti et al. | |
| 2004/0191119 A1* | 9/2004 | Zanzucchi | G01N 21/78 |
| | | | 422/504 |
| 2006/0217636 A1* | 9/2006 | Braig | A61B 5/1455 |
| | | | 600/583 |
| 2007/0191702 A1* | 8/2007 | Yodfat | A61B 5/14546 |
| | | | 600/347 |
| 2008/0319287 A1* | 12/2008 | Gross | A61K 49/0045 |
| | | | 435/14 |
| 2012/0059232 A1 | 3/2012 | Gross et al. | |
| 2013/0006069 A1 | 1/2013 | Gil et al. | |
| 2016/0058354 A1* | 3/2016 | Phan | A61B 5/157 |
| | | | 600/362 |
| 2017/0135614 A1 | 5/2017 | Klueh et al. | |

OTHER PUBLICATIONS

Supplementary Extended European Search Report dated Jul. 25, 2023, European Application No. 20853011.3, pp. 1-7.

* cited by examiner

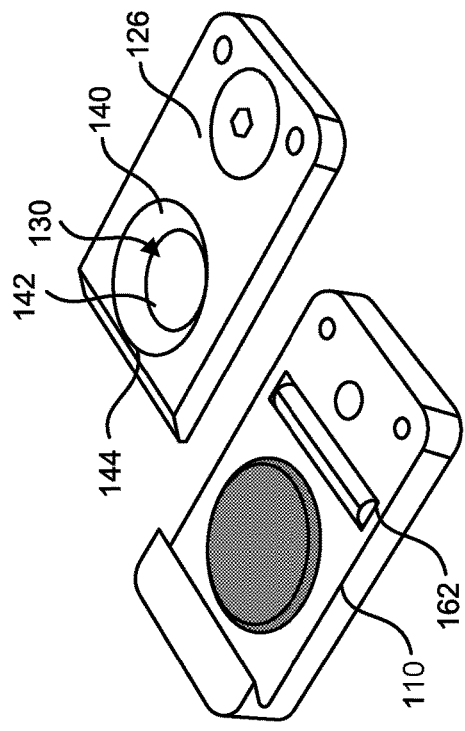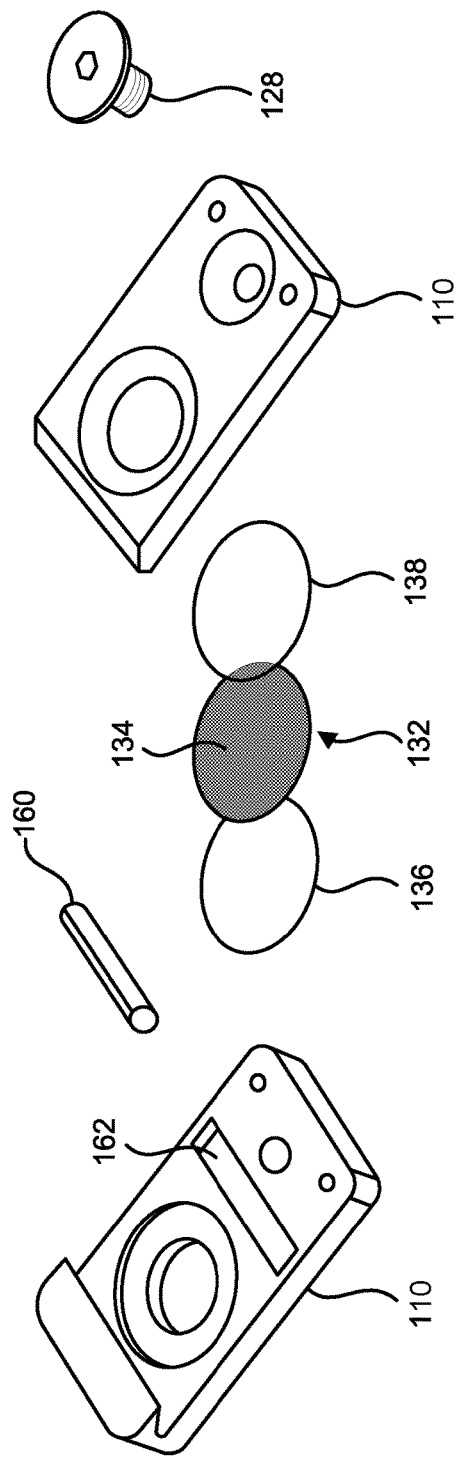

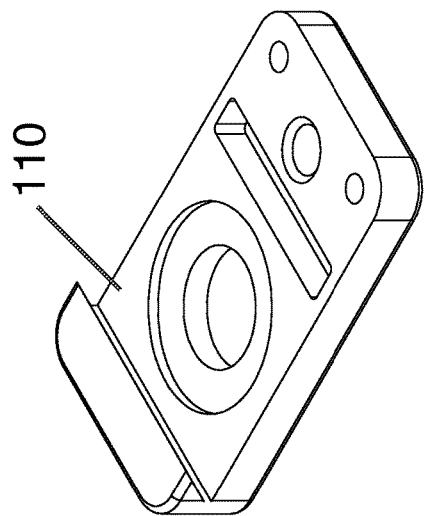
FIG. 6A
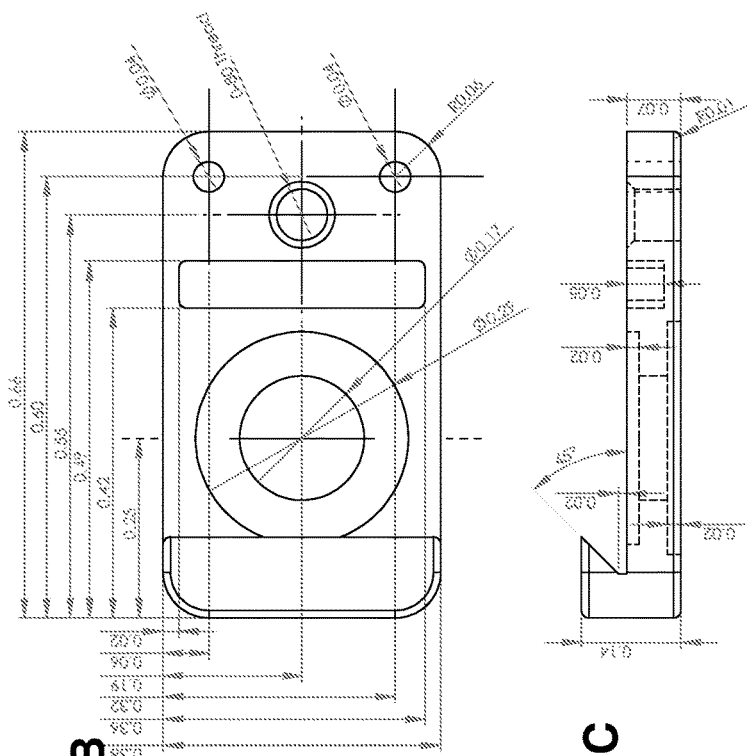
FIG. 6B
FIG. 6C
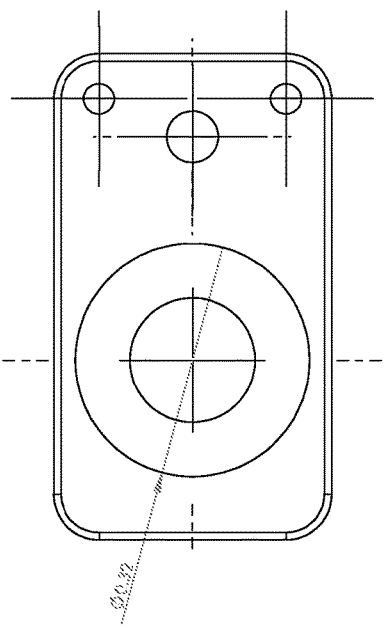
FIG. 6D

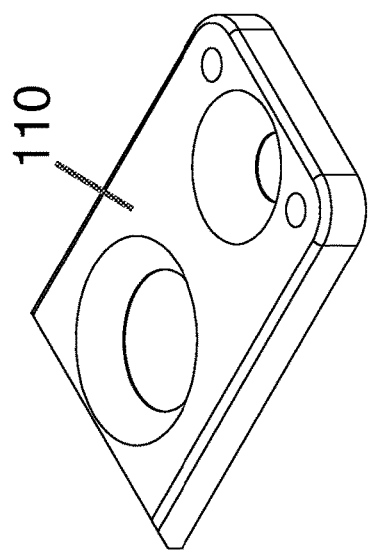
FIG. 7A
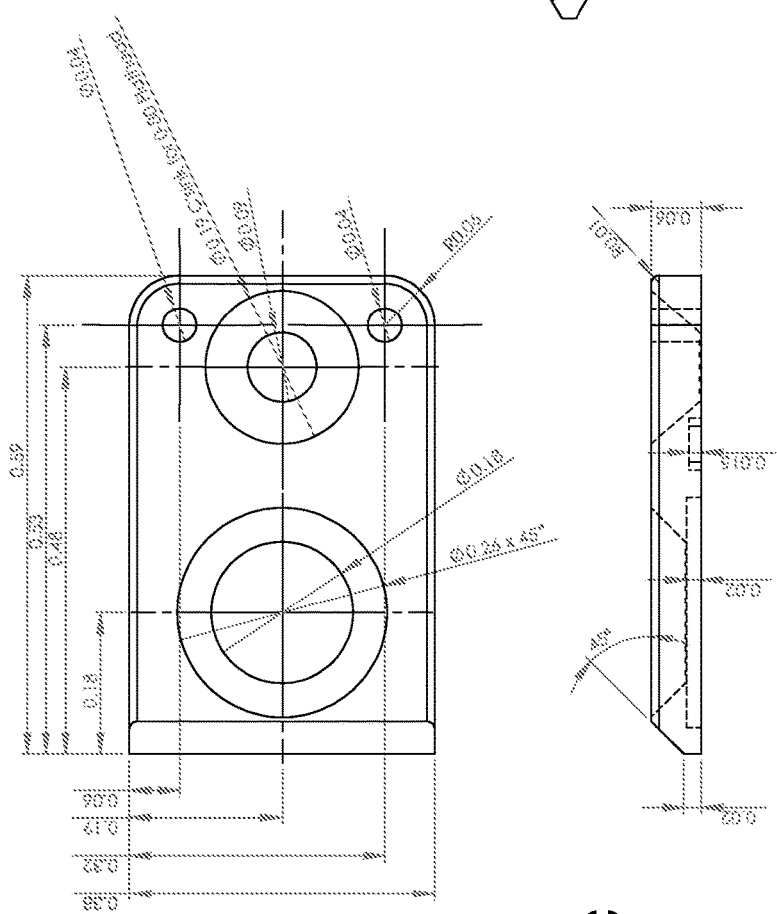
FIG. 7B
FIG. 7C
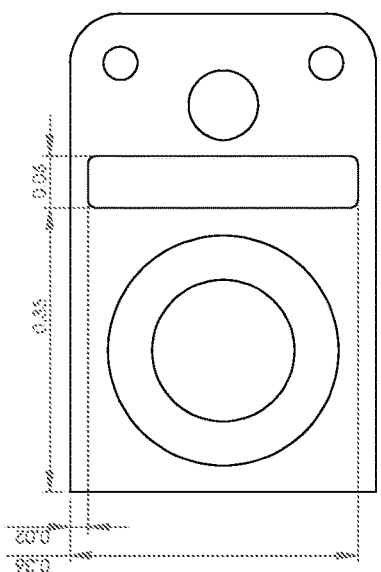
FIG. 7D

WEARABLE DEVICES FOR MONITORING PHYSIOLOGICAL CHANGES AND METHODS OF USE

FIELD OF THE DISCLOSURE

The present disclosure relates to system or devices with wearable devices having one or more sensors, and more particularly, to system or devices with wearable devices suitable for monitoring physiological changes within the body.

BACKGROUND

There are a wide variety of electronic and mechanical devices for monitoring and treating patients' medical conditions. In some examples, medical devices such as biosensors may be surgically implanted to the patient depending on the underlying medical condition being monitored or treated. Such medical devices are capable of monitoring patient's physiological changes such as blood pressure, heart rate, ECG, body temperature, glucose levels, gene and protein changes, local cellular changes that reflect systemic disease or change in health status or other body parameters. In some cases, physicians may use medical devices alone or in combination with drug therapies to treat patient medical conditions.

Wearable biosensors that can monitor a patient's physiological changes can significantly improve the ability of physicians to treat these otherwise life-threatening conditions. Such devices, however, come with certain limitations, namely that they need to be implanted. Implanted devices require a patient to have the device surgically implanted within them which could result in hospitalization, complications, and down-time following the procedure. Consequently, there is a need for wearable devices and the system for networking the wearable devices to aid in monitoring patients' physiological conditions.

SUMMARY

There is a need for improved wearable devices and methods for monitoring physiological changes a patient. The present disclosure is directed toward further solutions to address this need, in addition to having other desirable characteristics.

In accordance with an example embodiment of the present disclosure, a wearable device for use in monitoring physiological changes in the patient is disclosed. The device can include a housing adapted to being secured to a patient's body, the housing comprising a needle configured for fluid contact with a bodily fluid under a skin surface; a chamber having a cell layer and configured to monitor physiological changes in the bodily fluid and to generate one or more signals associated with the physiological changes; and a reader for detecting and/or decoding signals from the cell layer to monitor physiological changes in the patient.

According to aspects of the present disclosure, the housing can be secured to the patient's body with a removable element. The removable element can be an adhesive tape.

According to aspects of the present disclosure, the chamber can be secured within the housing.

According to aspects of the present disclosure, the chamber can include a biologic component. The biologic component can include a cell layer having cells pre-positioned on or in the device prior to implantation. The pre-positioned cells can respond to a physiological signal from the patient.

In accordance with yet further aspects of the present disclosure, the chamber can further include a first membrane and a second membrane on either side of the biologic component. The first membrane can be a non-porous membrane on which the cell layer is pre-positioned. The first membrane can be made from glass. The second membrane can be a porous membrane that allows for select fluid and nutrients to pass to the cell layer.

In accordance with yet further aspects of the present disclosure, the chamber can further include an electronic component. The electronic component can be a light source. The light source can illuminate light onto the cell layer thereby causing certain cells within the cell layer to emit light.

In accordance with yet further aspects of the present disclosure, the chamber can further include a microfluid pump for pumping fresh fluid over the cells.

In accordance with yet further aspects of the present disclosure, the chamber can further include a waste fluid chamber. The waste fluid chamber can receive and store the fluid after it has passed over the cells.

In accordance with yet further aspects of the present disclosure, the device can be capable of engaging in a two-way communication through transmission of one of more signals with a second device.

In accordance with yet further aspects of the present disclosure, the device can further include a temperature sensor for monitoring temperature changes in the cells.

In accordance with yet further aspects of the present disclosure, the device can further include a temperature controller for adjusting the temperature to a desired parameter.

In accordance with an example embodiment of the present disclosure, a system for monitoring physiological changes in the patient is disclosed. The system can include a wearable device for use in monitoring physiological changes in the patient, the device including a housing adapted to being secured to a patient's body, the housing comprising a needle configured for fluid contact with a bodily fluid under a skin surface; a chamber having a cell layer and configured to monitor physiological changes in the bodily fluid and to generate one or more signals associated with the physiological changes; and a reader for detecting and/or decoding signals from the cell layer to monitor physiological changes in the patient; and a second device for detecting and/or decoding the one or more signals to monitor physiological changes in the patient.

In accordance with an example embodiment of the present disclosure, a method for monitoring physiological changes in the patient is disclosed. The method can include providing a wearable device for use in monitoring physiological changes in the patient, comprising: a housing adapted to being secured to a patient's body, the housing comprising a needle configured for fluid contact with a bodily fluid under a skin surface; a chamber having a cell layer and configured to monitor physiological changes in the bodily fluid and to generate one or more signals associated with the physiological changes; and a reader for detecting and/or decoding signals from the cell layer to monitor physiological changes in the patient; transmitting one or more signals from the wearable device to a second device that is capable of detecting and/or decoding the one or more signals to monitor physiological changes in the patient; and detecting and/or decoding the one or more signals to monitor physiological changes in the patient.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 3A, FIG. 3B, and FIG. 3C are perspective views of a wearable device in accordance with an embodiment of the present disclosure.

FIG. 6A, FIG. 6B, FIG. 6C, and FIG. 6D are drawings of a wearable device in accordance with an embodiment of the present disclosure.

FIG. 7A, FIG. 7B, FIG. 7C, and FIG. 7D are drawings of a wearable device in accordance with an embodiment of the present disclosure.

DETAILED DESCRIPTION

Figure 1:
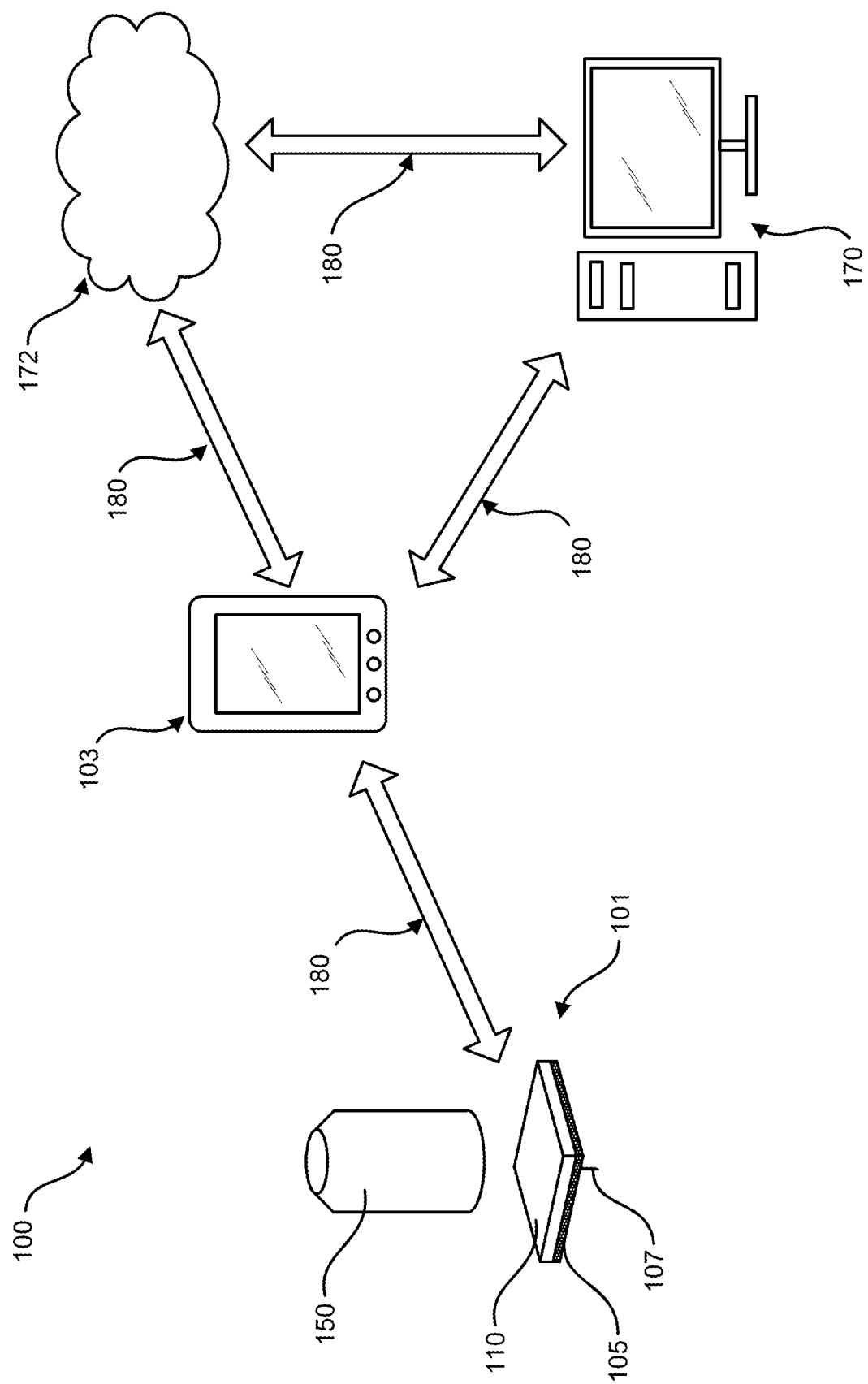
FIG. 1 is a high-level diagram depicting an example embodiment of a system for monitoring physiological changes within the body, data acquisition, and/or processing.

An illustrative embodiment of the present disclosure relates to a wearable device suitable for monitoring physiological changes within the body. The device can include a housing adapted to being secured to a patient's body, the housing having a needle configured for fluid contact with a bodily fluid under a skin surface to monitor physiological changes in the patient.

As used herein, the term "wearable device" is anything that can be worn by an individual and that has a back side that in some embodiments contacts a user's skin and a face side. As used herein, the term "wearable" refers to a device that is removable, detachable, or otherwise is not surgically implanted into a patient. The term "wearable device" can also be a monitoring device if it includes monitoring elements.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved.

As used herein, the term "user" includes but is not limited to a person, under a physician's care, whose physiological changes will be measured.

By "patient" or "subject" or "individual" or "animal" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

FIG. 1 through FIG. 9, wherein like parts are designated by like reference numerals throughout, illustrate an example embodiment or embodiments of a wearable biosensor suitable for monitoring physiological changes within the body, according to the present disclosure. Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

As FIG. 1 illustrates, embodiments of a system 100 for use in monitoring physiological changes in the patient may comprise wearable devices 101, e.g., biosensors, for monitoring physiological changes within the body. A number of systems and methods have been developed for the automatic monitoring of bodily fluid such as in the blood stream, in interstitial fluid ("ISF"), dermal fluid of the dermal layer, or in another biological fluid. Some of these systems are configured so that at least a portion of a sensor is positioned below a skin surface of a user, e.g., in a blood vessel or in the subcutaneous tissue of a user, to obtain information about at least one analyte of the body.

The wearable medical device 101 may be an ambulatory device (e.g., a device that is capable of and designed for moving with the patient as the patient goes about his or her daily routine). In an embodiment, the device 101 can be worn by the patient in a continuous (e.g., substantially continuous) fashion, and the patient's physiologic state can be continuously monitored, e.g., monitoring the patient's physiological changes through its sensors. In some embodiments, the continuous use can be substantially or nearly continuous in nature. That is, the wearable medical device 101 may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device 101 can be configured to be worn by a patient for as many as 24 hours a day. In some implementations, the patient may remove the wearable medical device for a short portion of the day (e.g., for half an hour to bathe).

The wearable device 101 is also capable of extended use, and in some implementations, extended long-term use. For example, the wearable device can be configured to be used by the patient for hours, days, weeks, months, or even years. In some implementations, the extended use may be continuous in nature. The use (e.g., the continuous and/or extended use) of the wearable device can include continuous wear by the patient, continuous attachment to the patient, and/or continuous monitoring of the patient. The wearable device 101 may carry out its monitoring in periodic or aperiodic time intervals or times. For example, the monitoring during intervals or times can be triggered by a user action or another event. For example, one or more durations between the periodic or aperiodic intervals or times can be user-configurable.

System 100 can have a first device 101 that produces a signal and a second device 103 spaced apart from the first device 101 for receiving the signal that communicate with each other over a local communication path (or link), which can be wired or wireless, and uni-directional or bi-directional. In embodiments where the communication path is wireless, any near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants. In an embodiment, the signals may be optical signals or light signals. As used herein, "optical signals" may refer to infrared light, visible light, and ultraviolet light. In accordance with an embodiment of the present disclosure, the signals may be infrared light. In accordance with an embodiment of the present disclosure, the signals may be visible light. In accordance with an embodiment of the present disclosure, the signals may be ultraviolet light. In accordance with an embodiment of the present disclosure, the signals may include infrared light, visible light, ultraviolet light, electromagnetic radiation, radio waves, microwaves, X-rays, gamma rays, ultrasonic signals or combinations thereof. It should be appreciated that other signals known in the art may also be included In an embodiment, the signals, e.g., optical signals, may travel through the body with minimal interference from the surrounding tissues or organs. For instance, the signals, e.g., optical signals, may travel through muscles, organs such as lungs and the heart, bone, cartilage, or any other tissues in the body while experiencing minimal interference and/or loss in wavelength frequency. In an embodiment, it is expected that the loss in wavelength frequency will be less than 10%, less than 9%, less than 8%, less than 7%, less than 6%, less than 5%, less than 4%, less than 3%, less than 2%, or less than 1%. It should be appreciated that the amount of loss can vary based on a number of factors. For instance, the amount of loss can depend on the type of signal and/or the type of wavelength selected. In addition, the amount of loss may depend on the amount of absorption, diffusion and/or scatter. It should be appreciated by one skilled in the art, however, that the amount of loss will be minimal and will not impact the operation of the disclosure of the present application.

In embodiments, the signal is encoded using frequency and/or amplitude modulation. In this way, the signals, e.g., optical signals, may carry data such as blood pressure, heart rate, ECG, body temperature, glucose levels, gene and protein changes, local cellular changes that reflect systemic disease or change in health status or other body parameters to second device 103. In an embodiment, the signals may have a wavelength frequency in a range of approximately $1 \times 10^{-8}$ to $1 \times 10^{-1}$ Hz. Of course, it should be appreciated to anyone skilled in the art that the wavelengths may vary.

In an embodiment, the first device 101 can monitor the integrated biologic tissue (biopsied and grown cells) and notice if there is a change in electrical activity of the cell, increased contraction or stretch activity, or metabolic activity as it responds to the physiologic signal of interest. In one embodiment, the direction of the signals is reversed. In one embodiment, the signal is encoded using frequency and/or amplitude modulation. In this way, the signal may carry data such as blood pressure, heart rate, ECG, body temperature, glucose levels, gene and protein changes, local cellular changes that reflect systemic disease or change in health status or other body parameters to second device 103.

In one embodiment, both the first device 101 and the second device 103 are situated outside the body. For instance, the first device 101 is external to the body but secured to the body while the second device 103 is spaced apart from the body. In another embodiment, only one of the components is external to the individual while the other is internal in the body. For instance, the first device 101 is internal in the body while the second device 103 is external to the body. In another embodiment, there may be any number devices implanted within the body or situated external to the body. The first device 101 may be the same or substantially the same as that described in U.S. Pat. Nos. 8,024,020; 8,849,416; 8,938,300 and U.S. patent application Ser. No. 13/212,804 all of which are hereby incorporated by reference.

In an embodiment, the second device 103 may be the same or substantially the same as the first device 103. In another embodiment, the second device 103 may be different from the first device 103. For instance, the second device 103 may be a pace-maker, a glucose monitor pump, an insulin pump, a neurostimulator, a defibrillator or any other medical device that can be implanted within or carried on a person.

In an embodiment, the first device 101 may include a housing 110 for containing the system for monitoring physiological changes in the patient's bodily fluid. The housing 110 may be adapted to being secured to a patient's body. In an embodiment, the housing 110 can have any suitable shape and size. The housing 110 may be oval, tubular, rectangular, square, pentagonal, hexagonal, or any other shape as long as the housing 110 is able to be secured to a patient's body. To minimize discomfort and prevent sharp edges or obstruction points to tissue or surrounding materials as they are engaged and moved, housing 110 may be as thin as possible and the edges may be radiused or chamfered. The housing 110 can be constructed of any materials suitable to form a structure, such as stainless steel, plastic, polyamide, Teflon, polymers, ceramic, or other synthetic or biological materials, such as, but not limited to, cartilage. In one embodiment, the materials have sufficient stiffness to maintain their own respective column and are able to increase the flexural rigidity of the probe to which they have been applied to.

The housing 110 may be placed anywhere on the body and may be placed in direct contact with the skin. In an embodiment, the housing 110 may be secured to the skin with an adhesive element 105. The adhesive element 105 contains an adhesive layer for attachment to a skin surface of the body of the patient. Other forms of body attachment to the body may be used, in addition to or instead of adhesive. For example, other forms of attaching the housing 110 to the skin may include, but is not limited to, the use of a halter, carrier, arm, wristband, belt, leg or abdomen banding. The device 101 may also be situated apart from the skin and the body through the use of extended fluidic tubing to allow for use in a hospital bed or other method where the device is not directly attached to the body when in use for a patient that may not be ambulatory.

Within housing 110, the system for monitoring physiological changes in the patient's bodily fluid can be found. In many embodiments, the system can be sterilized and sealed within its housing 110 such that the interior of the housing 110 is inaccessible to the external material environment (e.g., air and the user). In such a configuration the user does not have access to the components of the system. The system can be coupled with a sensor 107 that can extend through an adhesive element 105 and project away from housing 110. Sensor 107 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user.

In one embodiment, the sensor 107 is a needle. The sensor 107 can be inserted into the patient subcutaneously or intravenously. In an embodiment, the wearable device 101 is capable of being removed from the patient's body. Once removed, the device 101 can either be reapplied or a new device 101 can be applied to the patient. When the sensor 107 is inserted subcutaneously, removable of the device 101 means that the entire device 101, including the sensor 107, is removed from the patient's body. On the other hand, when the sensor 107 is inserted intravenously, removal of the device 101 means that sensor 107 is capable of detaching from the intravenous line that was inserted into the patient. Alternatively, removal of the device 101 means that device 101 is detached from the sensor 107 which is left behind with the intravenous line.

In one embodiment, the first device 101 and its components can be applied to the body with a mechanical applicator 150 in one or more steps or in any other desired manner. Once the user has chosen an application site, the device 101 is secured to the body. To secure the device 101, the user places the mechanical applicator 150 on the skin of the insertion site and then applies a force to install the device 101. The mechanical applicator 150 is driven to insert the distal end of the sensor 107 through the user's skin, adhere the device 101 to the skin surface, and separate the device 101 from the mechanical applicator 150. In some embodiments, the user performs the application operation by applying force to the applicator where the force applied is a single, continuous pushing motion along the longitudinal axis of the applicator that once started, causes the applicator to perform the application operation such that the applicator does not stop operation until completion. In an embodiment, an adhesive element 105 of the device 101 does not contact the user until the application operation is performed. So, the even after the applicator has been placed on the skin, the applicator can be moved to a different location up until the application operation is performed without damage to the apparatus or other system components.

In accordance with various embodiments, the housing 110 and device 101 can be made as a whole piece or segment, or in separate segments that can be coupled together, (i) mechanically, (ii) by adhesion, (iii) by heat staking, (iv) with magnets, (v) other coupling mechanisms, and the like.

After activation, the first device 101 can wirelessly communicate the collected bodily fluid data (such as, for example, data corresponding to monitored physiological changes to second device 103 where, in certain embodiments, it can be algorithmically processed into data representative of the physiological changes of the user and then displayed to the user and/or otherwise incorporated into a monitoring regime for a specific condition.

As shown in FIG. 1, the system 100 can also include a second device 103 that receives physiological data from the first device 101 and detects, decodes, processes, and/or displays that physiological data, in any number of forms, to the user. In an embodiment, the second device 103 may decode or demodulate the signal 180 to receive the data encoded within the signal 180 and may compare the signal 180 to a reference signal to diagnose the disease or condition. In response to the detected signal 180, the second device 103 may initiate an action. The action can include adjusting the patient's medical treatment (i.e. drug delivery), activate an alarm, send information to the physician, etc. It should be appreciated that signal 180 can be uni-directional or bi-directional.

This second device 103, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in such monitoring systems.

In one embodiment, the second device 103 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with network connectivity for data communication over the internet or a local area network (LAN).

Second device 103 can include a display that outputs information to the user and/or to accept an input from the user (e.g., if configured as a touch screen), and one or more optional user interface components, such as a button, actuator, touch sensitive switch, capacitive switch, pressure sensitive switch, jog wheel or the like. Second device 103 can also include one or more data communication ports for wired data communication with external devices such as a computer system 170 or a cloud 172.

Computer system 170 may be a personal or laptop computer, a tablet, or other suitable data processing device. Computer system 170 can be either local (e.g., accessible via a direct wired connection such as USB) or remote to second device 103 and can be (or include) software for data management and analysis and communication with the components in system 100.

Computer system 170 can be used to perform authentication of the first device 101 and/or second device 103, used to store confidential data received from devices 101 and/or 103, used to output confidential data to devices 101 and/or 103, or otherwise. Computer system 170 can include one or more computers, servers, networks, databases, and the like. Computer system 170 can be within the possession of the manufacturer or distributor of first device 101, either physically or virtually through a secured connection, or can be maintained and operated by a different party (e.g., a third party). Computer system 170 can be trusted in the sense that system 100 can assume that computer system 170 provides authentic data or information. Computer system 170 can be trusted simply by virtue of it being within the possession or control of the manufacturer, e.g., like a typical web server. Alternatively, computer system 170 can be implemented in a more secure fashion such as by requiring additional password, encryption, firewall, or other internet access security enhancements that further guard against counterfeiter attacks or attacks by computer hackers.

The processing of data and the execution of software within system 100 can be performed by one or more processors of first device 101, second device 103, and/or computer system 170. For example, raw data measured by sensor 107 can be algorithmically processed into a value that represents the physiological level and that is readily suitable for display to the user, and this can occur in first device 101, second device 103, or computer system 170. This and any other information derived from the raw data can be displayed in any of the manners described above on any display residing on any of first device 101, second device 103, or computer system 170. The information may be utilized by the user to determine any necessary corrective actions to ensure the analyte level remains within an acceptable and/or clinically safe range.

Figure 2:
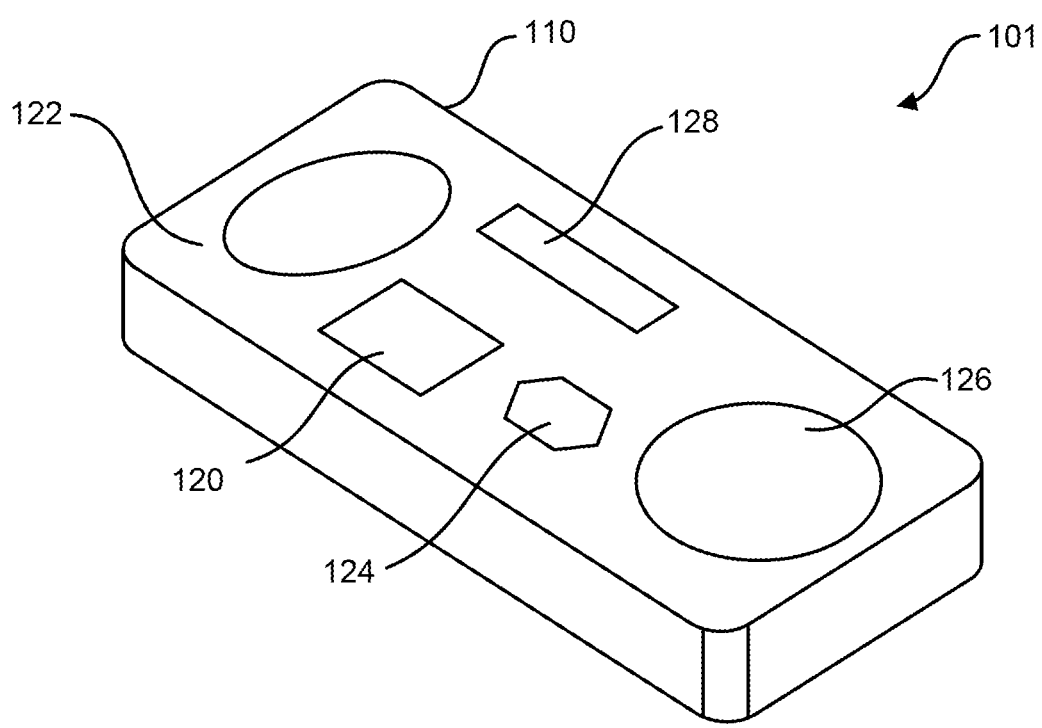
FIG. 2 is a drawing depicting a wearable device in accordance with an embodiment of the present disclosure.
Figure 4:
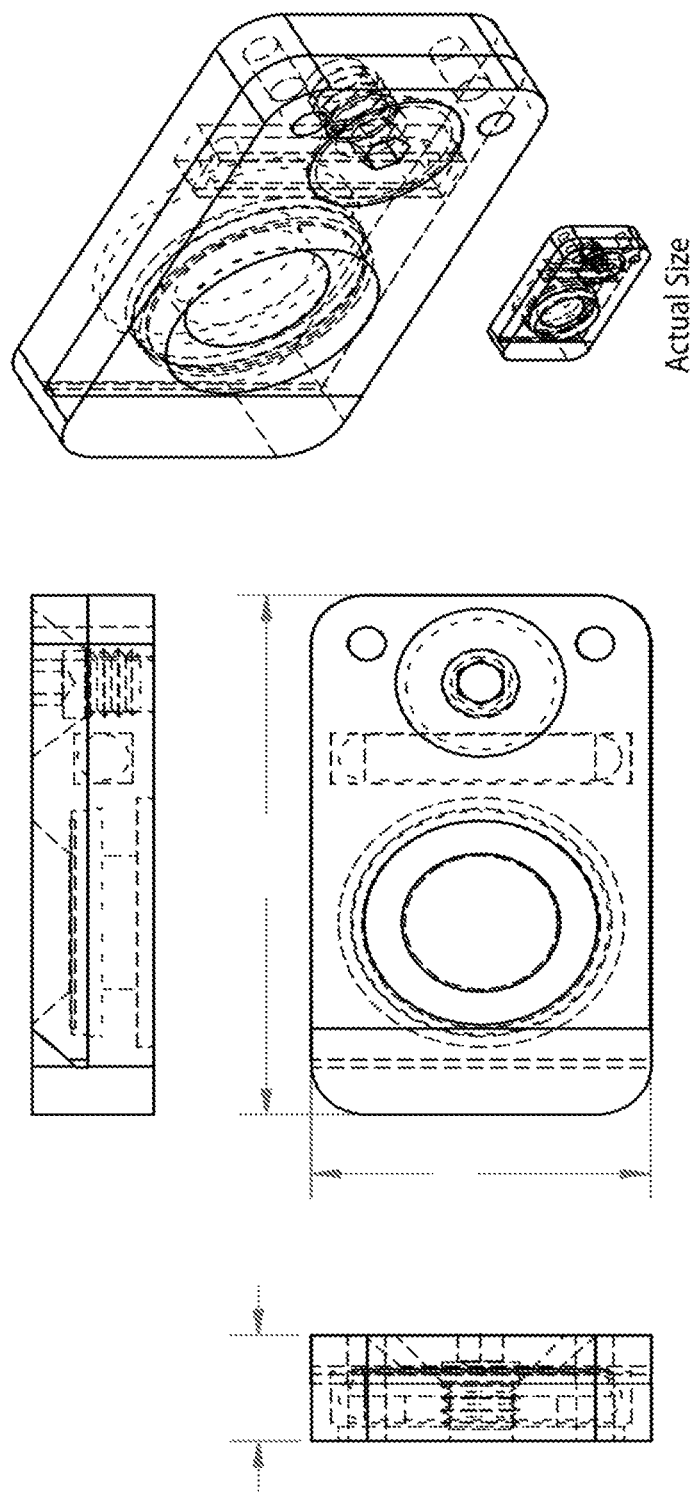
FIG. 4 is a drawing of a wearable device in accordance with an embodiment of the present disclosure.
Figure 5B:
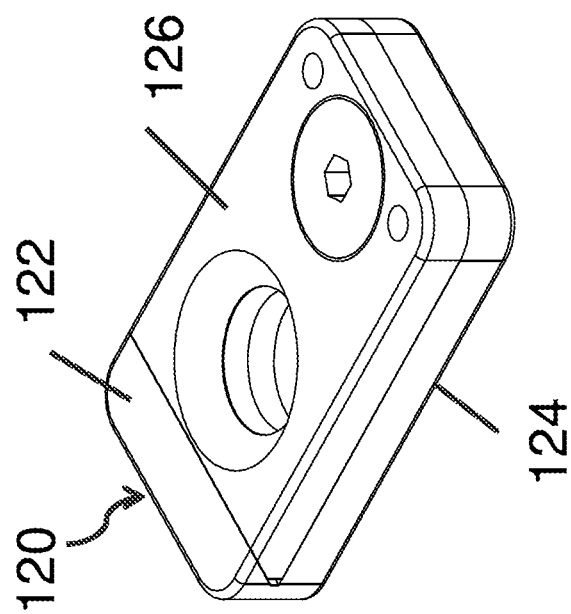
FIG. 5A and FIG. 5B are drawings of a wearable device in accordance with an embodiment of the present disclosure.
Figure 5A:
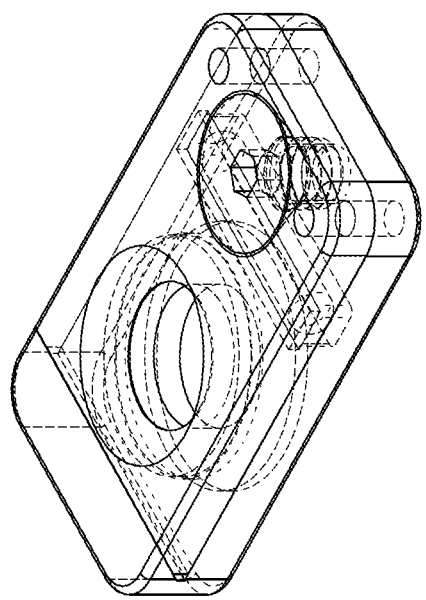

FIG. 2 is a drawing of housing 110 with its components for monitoring physiological changes in the patient's bodily fluid. In an embodiment, housing 110 may include a chamber 120, an electronics source 122, a microfluidic pump 124, a waste fluid chamber 126, and a power source 128.

FIG. 3A, 3B, 3C, 3D, 4, 5A, 5B, 6A, 6B, 6C, 6D, 7A, 7B, 7C, and 7D show various illustrations of chamber 120. As illustrated in FIG. 3A, the chamber 120 may include at least one opening 130. The opening 130 may be circular, rectangular, square, pentagonal, hexagonal, or any other shape. In one embodiment, the opening 130 is circular. The opening 130 may be any size appropriate for the chamber 120. In an embodiment, the diameter of the opening 130 ranges from about 0.10 mm and about 0.40 mm. As shown in FIG. 6B, the diameter is about 0.17 mm in diameter. Chamber 120 may be substantially as shown in U.S. patent application Ser. No. 16/410,294.

In an embodiment, the chamber 120 may include a biologic component 132 situated within the opening 130 in the body. In an embodiment, the biologic component may include cells 134 pre-positioned on or in the device prior to implantation. The pre-positioned cells 134 may be adapted to respond to a physiological signal from a patient. In one embodiment, the cells 134 may be from the target site. In another embodiment, the cells 134 may be from other sites.

The cells 134 may be placed in one layer, two layers, or multiple layers. Furthermore, the cells may be placed within three-dimensional (i.e., multi-layered) matrices and not limited to such a layer on a two-dimensional plate. The cells 134 are placed so that the cells 134 have a thickness of generally no more than about 0.5-1 mm so that the cells receive ample nutrients including oxygen exposure.

The cells 134 are cells of interest (such as, but not limited to, cardiac, vascular, gastrointestinal, bone, tissue, or cartilage, depending on the application) which are cultured or otherwise obtained from the patient and grown in a chamber. The internal environment and architecture of the chamber is optimized to support the specific cells of interest and may include but not limited to, natural and synthetic matrix materials used for scaffolding and support of cells 134. Since the cells are cells of interest from the patient, they are able to survive once implanted. The chamber 120 is a biocompatible structure that allows the healthy growth and adhesion of cells. Although synthetic and/or naturally occurring substances are preferred, any substance can be used that has biocompatibility with the target cells and maintains cellular architecture intact while allowing cells to grow and live within its environment.

The cells 134 are selected based on their ability to detect and respond to the physiologic signal of interest. For example, if a response to circulating chemical messengers such as catecholamines is required information, then skeletal muscle may be used. Accordingly, those cells eliminate the need for a separate sensor to detect the desired chemical messenger. In this setting, the muscle is biopsied from the arm or leg and placed into an environment that allows separation of the cells in an atraumatic fashion so as to minimize damage. The cells are then grown onto the device. The site of growth includes direct contact with an array of electrodes or Micro-electromechanical devices. The electrode array interface may be in a single plane or the electrodes distributed within a three-dimensional architecture so that the cells are in direct contact with a variety of electrodes. When the cells have matured and attached themselves to the electrode/sensor circuitry/MEMs, then the device is prepared for implantation within the same person from whom the cells were obtained. Alternatively, the cells may be from another human or non-human source and produced in such a way to be compatible with the person in whom it is implanted. This minimizes scar formation and rejection.

In this scenario, the cells 134 respond to increase in catecholamines by increasing their frequency of firing as well as strength of contraction, which is measured by a shear stress recording sensor, pressure via pressure transducer, and the rate of change of the mechanical conformational changes. The change in shear stress/pressure and/or electrical activity (amplitude and frequency) can be detected. The electrical activity is also recorded if it is the desired signal or cellular response that is used as a marker. The first device 101 then transmits the detection to an external controller or may have its own controller that either stores and/or acts on the information by emitting an electrical stimulus to inhibit or stimulate the target organ in which the device is implanted. The data may also be wirelessly communicated, for example using ultrasonic sound, to another networked implanted or external device that then performs the intervention that may consist of electrical stimulation or trigger an infusion of a substance by an implanted or external pump.

Within the chamber 120, the cells 134 are situated between a first 136 membrane and a second membrane 138 as shown in FIG. 3C. The first membrane 136 and second membrane 138 function to keep the cells 134 positioned in one place and prevent them from being distorted. In one embodiment, the first membrane 136 is non-porous. The first membrane 136 is positioned adjacent to or abutting the housing 110 and provides an interface between the housing 110 and the cells 134 it contacts. In one embodiment, the first membrane 136 is made of glass. The second membrane 138 is positioned adjacent to the human body and provides an interface between the human body and the cells 134 it contacts. In contrast to the first membrane 136, the second membrane 138 may be porous to allow for select fluid and nutrients to pass to the cells 134.

To maintain the positioning of the cells 134 between the first membrane 136 and second membrane 138, the opening of the chamber 120 may be in the form of a crater, as shown in FIG. 3A and FIG. 3B. In one embodiment shown in FIG. 3B, the crater shape may include walls 140 that extend from the base 142 of the crater to the top 144 of the crater. At the base 142 of the crater is the second membrane 138 which contains the layer of cells 134. The wall 140 acts to secure the cell layer within the biologic component and prevent distortion or migration of the cells. In one embodiment, the base 142 of the crater has a smaller diameter than the top 144 of the crater. In another embodiment, the base 142 of the crater has the same or substantially the same diameter as the top 144 of the crater. In one embodiment, the wall 140 may have angled sides in relation to the biologic material 132. In one embodiment, the sides of the wall 140 may be angled between about 30 degrees and 90 degrees. In one embodiment, the sides of the wall 140 may be angled at about 45 degrees.

In addition, an optional coating may be applied to the outer surface of cells 134 or to the first membrane 136 or second membrane 138. The coating may inhibit the formation of scar tissue or fibrotic growth over the first device 101. In addition, a coating may include substances to promote growth of blood vessels around the device to enhance or optimize contact with blood/fluid borne signals. In another embodiment, the coating may be a drug-eluting coating which delivers drug to surrounding tissue at predetermined rates. Steroids dilute over time and eventually disappears.

Figure 8A:
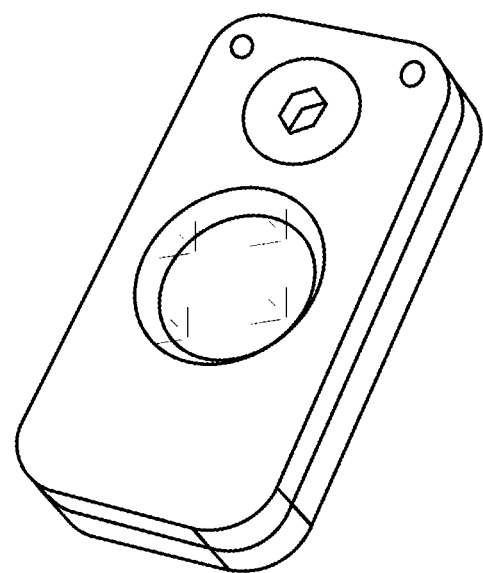
FIG. 8A and FIG. 8B are drawings of a wearable device in accordance with an embodiment of the present disclosure.
Figure 8B:
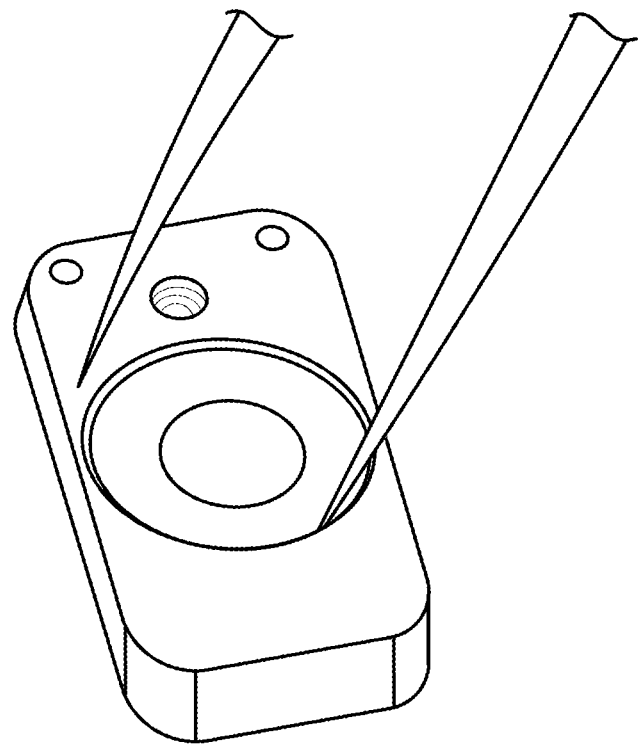
Figure 9:
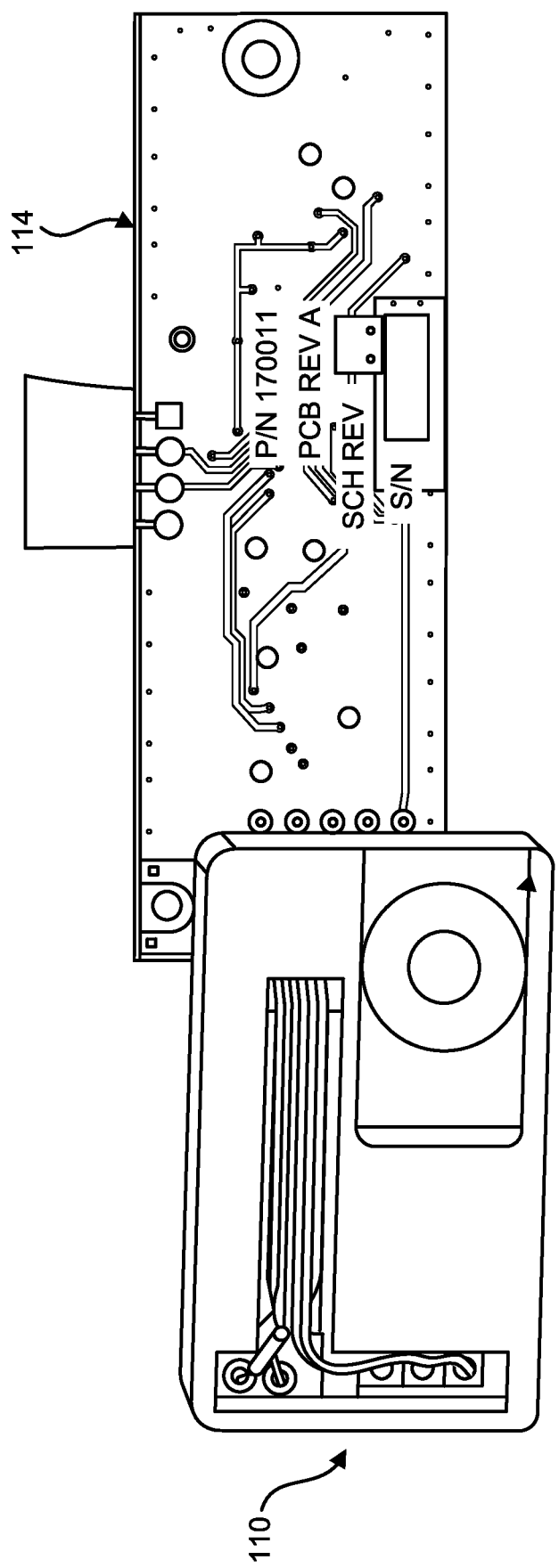
FIG. 9 is a drawings of a wearable device in accordance with an embodiment of the present disclosure.

Referring now to FIG. 9, the first device 101 may further include an electronic component 114. In an embodiment, the electronic component 114 may include a light source (not shown) for shining light onto the cells 134 through the first membrane 136 thereby causing certain cells 134 to emit light as shown in FIG. 8A. In FIG. 8A, an excitation signal in the form of light is emitted by an excitation emitter (not shown) that enters the cells 134. The cells 134 have surface receptors that are integral to the membrane proteins of the cell. When a signal (e.g., light) interacts with the receptors, they form a triggering mechanism that stimulates a signaling response that may also include DNA/RNA response that, in turn, causes a protein to be synthesized by the cells 134. It may also trigger direct protein conformational changes independent of protein synthesis that can be detected. That protein has certain physical properties, including the ability to fluoresce upon absorption of certain wavelengths of light. The more protein present in the cells 134, the higher the fluorescence intensity. In an alternate embodiment, a detection protein, like green fluorescent protein (GFP) from jellyfish, may be attached to the protein (other detection substances may also be used). In an alternate embodiment, an intracellular dye may also be used instead of GFP.

To detect and/or decode light emitted from the cells 134, the electronic component 114 of the first device 101 may further include a reader (not shown). The reader detecting and/or decoding light emitted from the cells 134 to monitor physiological changes in the patient. The cells 134 provide sensing and individual cellular responses that can be measured by the reader, such as pressure and deformation changes in cellular structure, photo-optical changes elicited by the cell. The ability to detect and measure these various cellular responses, the first device 101 provides a broad range of clinical application for which it can be used. The first device 101 such as that of the present disclosure can be individually tailored to measure different physiological changes in the patient.

The first device 101 may further include a microfluidic pump 124 to allow for fresh fluid to flow over the cells 134. In an embodiment, the fluid may flow continuously over the cells 134 or it may flow non-continuously. A microfluidic pump 124 generally refers to any structure or group of structures capable of applying pressure to a fluid, and/or facilitating the flow of fluid in one or more desired directions in a microfluidic device. A number of the valve structures can be placed in series and interconnected by microchannels to form a micro pump 124 in accordance with an embodiment of the present disclosure. The pump 124 may be operated in peristaltic-like cycles. When activated in the proper sequence, fluid will be forced through the pump structure.

In accordance with the embodiment depicted in FIG. 2, the first device may further include a waste fluid chamber 126 for receiving and storing the fluid after it has passed over the cells 134. In accordance with an embodiment of the present disclosure, the fluid that leaves the patient's body is never returned or recycled back into the body. Instead, the fluid is collected in the waste fluid chamber 126 until it is discarded. In this way, the device 101 of the present disclosure is a one-way device. The waste fluid chamber 126 can be of any shape and size as long as it fits within the housing 110.

In an embodiment, the waste fluid chamber 126 can be removable and replaceable so that the contents of the chamber 126 can be discarded and a new or empty chamber 126 can be reinserted by the user. In an embodiment, the waste fluid chamber 126 can include a sensor that is capable of monitoring and detecting the amount of fluid in the waste fluid chamber 126 and subsequently alerting the user when the fluid needs to be discarded.

The first device 101 may further include a power source 128. In an embodiment, the power source 128 may be a battery configured to provide power to one or more components integrated in the device 101. In an embodiment, the power source 128 can include a rechargeable multi-cell battery pack. In one example embodiment, the power source 128 can include three or more 2200 mAh lithium ion cells that provide electrical power to the other device components within the device 101. For example, the power source 128 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the device 101. It should be appreciated, however, that other power sources may also be used.

In an embodiment, the power source 128 may be situated within the housing 110. In such a configuration the user does not have access to power source 128. In an embodiment, the power source 128 may be removable. In an embodiment, the power source 128 can be rechargeable. In this manner, the power source 128 can be removed from the device 101 and can be recharged either wirelessly or can be recharged in a charging station connected to a source of electricity.

In accordance with an embodiment of the present disclosure, the power source 128 can be put into a sleep state when not actively used in order to preserve power. A wake-up feature allows the power source 128 and other electronics of the device 101 to "sleep" during non-use or and is initiated into the "wake up" mode by certain predestinated events. For example, as the first device 101 comes out of the factory, the first device 101 can be in a dormant state where only a very low power drain exists on the power source 128. When the user is ready to use a first device 101 for the first time, the first device 101 can be brought out of its dormant state into a relatively higher power state, or a full power state (e.g., awakened or activated) by a mechanism activated by the user. This enhances both the shelf and operating life of first device 101.

The first device 101 may further include a temperature sensor and controller (e.g., a thermocouple, a thermistor, a resistance temperature device, an optical or infrared sensor, combinations of the same or the like) that is capable of maintaining the cells in the proper temperature for functioning. In these devices an electrical parameter-typically voltage or resistance-changes in relation to a temperature change. A circuit is configured to measure the change in the parameter to derive the temperature change or temperature. Wires are used to connect to the device to the electrical circuit and transfer the data to a digital display. For an intravascular catheter the wires need to be reduced or eliminated in order to minimize the impact on the catheter performance. As used herein, a "temperature sensor" includes any temperature determination device/mechanism for measuring temperature and communicating temperature information to a controller and/or to a pump processor. In an embodiment, a temperature sensor may monitor for high temperature or low temperature signals and then instruct a controller to adjust the temperature to the desire amount. In this manner, the device 101 of the present embodiment can operate outside of the human body.

The first device 101 may further include radio frequency identification (RFID) tag 160 for remotely storing and retrieving data. An RFID tag 160 is a small object, such as an adhesive sticker, that can be attached to or incorporated into the first device 101 of the present disclosure. As shown in FIG. 3B and FIG. 3C, housing 110 may include a slot 162 for housing the RFID tag 160. There are passive and active RFID tags. Passive RFID tags are small devices that are generally used at shorter range and for simpler tracking and monitoring applications than active tags. Passive tags generally act over ranges up to 3-5 meters, and a few hundred are typically readable simultaneously within three meters of a reader. Because they are powered by radio waves from RFID tag reader, passive tags do not use a battery. Accordingly, these devices are generally inexpensive and smaller than active tags and can last long. Active RFID tags have a power source, such as a battery, and generally have longer range and larger memories than passive tags. For example, active tags generally act over ranges up to 100 meters, and thousands of tags are typically readable simultaneously within 100 meters of a reader. For more details on passive and active RFID tags, see http://RFID-Handbook.com, which is hereby incorporated by reference. It should be appreciated that any sort of identification tagging, including bar code or other electronic means, may also be used.

Accordingly, it is envisioned that the system 100 and the wearable medical device 101 for use with the systems and techniques as disclosed herein can be configured to monitor and/or treat a patient. For example, the wearable device 101 can be configured to monitor physiological signals from the patient, and on detecting a medical event based on the monitored signals, treat the patient as needed. As described herein, a treatment sequence can include detecting a treatable medical condition, preparing the device for the treatment of the condition, providing a notification to the patient and/or others about an impending treatment, and/or delivering the treatment when certain conditions are met.

In another embodiment, the system 100 may be used for drug release or drug delivery applications. Drug delivery may be accomplished by way of epidermal delivery, transdermal delivery, intravenous delivery, or any other know suitable delivery method that provides drug delivery via a wearable device, such as, for example, through a transdermal matrix or a needle. Further treatment may include instructions delivered via communications with providers or databases via the user interface of the disclosure. Treatment may be automated in some embodiments, or triggered by user or provider decision making, whether remote to the user or on-site. In this regard, drug delivery may be performed via a communications component that sends dosing instructions to a dispensing device (e.g., an insulin pump or a medication pump) which may be secured to a patient. In an embodiment, the second device 103 may be coupled to the drug dispensing device. In response to a signal 180, the second device 103 may instruct the drug dispensing device to release drugs into the body. Sensors may then detect the effectiveness of the drug and allow the user to trigger another dose release. Such systems may allow for patient targeted treatment. This may be particularly useful in chronically ill patients, such as diabetic patients or patients undergoing cancer treatment. It should be appreciated that signal 180 can be uni-directional or bi-directional.

In another application, the wearable device 101 may be used in health monitoring. Similar to the above application, the second device 103 may detect and decode the signal 180 and may store data on storage medium such as a flash card, hard drive, or other devices known to those of skill in the art and/or send the data to a base station, such as a computer, a smart phone, or cell phone. Depending on the complexity of the system setup the information may be forwarded directly to a physician's office or nurses' station, first responders, or other qualified personnel who may then review the data and access the best possible treatment path forward. It should be appreciated that signal 180 can be uni-directional or bi-directional.

In a further application, embodiments of the disclosed wearable device 101 could be used to diagnosis medical conditions. Currently, a health care professional may be able to diagnose conditions and diseases only after reviewing and analyzing data such as the results of blood work, x-ray, computed tomography or magnetic resonance imaging, etc. Without being limited to theory, it is believed that conditions or diseases may have distorted signal 180. In a healthy individual, the signal 180 may be transmitted differently than in an unhealthy individual. Using an embodiment of the disclosed system, differences in the signal 107 or rate of transmission may alert a health care professional of a possible injury, disease or condition.

The wearable device 101 of the present disclosure can also provide information for use by other medical devices, such as a cardiac ventricular assist device to alter its flows and parameters to maximize cardiac output. The wearable device 101 can alternatively be used to modulate blood pressure and central nervous system reflexes such as the baroreceptor reflex system from peripheral nervous system points or directly form the brain itself. It can also be used to predict events such as ventricular fibrillation or onset of seizure activity within the brain by detecting neuro-transmitter changes that can only be detected by biologic tissue.

The wearable device 101 of the present disclosure is able to stimulate tissue with a predetermined sub-threshold pacing and determine the response of the cells 134 to obtain data regarding the cells' perception of the body's physiologic processes. For example, a cell may slightly increase electrical frequency of depolarization in response to an event, but the first device 101 may increase the sensitivity of the detection by stimulating the cell 132 and study the response of the cells 132 to the stimuli as a way of interpreting the signal. The stimulation triggers a response from the cells depending on the application. That evoked response provides information about the conditions being sensed by the cells.

Advantages of the device 101 of the present disclosure includes the ability of the device 101 to continuously monitor physiological changes in the patient thereby providing more accurate information about the patient. This, in turn, improves the diagnosis and treatment of the patient by allowing it to be more personalized. In addition, the device 101 of the present disclosure can be secured to and/or removed from the patient by a medical professional during an office visit rather than through surgery. This minimizes the time, pain, and inconvenience associated with having a surgical procedure to install a medical device. In this way, the device 101 of the present disclosure is easy-to-use, reliable, and minimizes both user inconvenience and pain.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the disclosure. It is intended that the present disclosure be limited only to the extent required by the appended claims and the applicable rules of law.

It is also to be understood that the following claims are to cover all generic and specific features of the disclosure described herein, and all statements of the scope of the disclosure which, as a matter of language, might be said to fall there between.

What is claimed is:

1. A wearable device for use in monitoring physiological changes in a patient, comprising:
   a housing adapted to being secured to a patient's body, the housing comprising a needle which can be inserted into the patient subcutaneously or intravenously, and which is configured for fluid contact with a bodily fluid under a skin surface;
   a chamber situated within the housing, the chamber comprising:
   (i) a biological component, with a first membrane and a second membrane on either side of the biologic component, the biological component having a cell layer comprising cells, wherein the first membrane is a non-porous membrane on which the cell layer is pre-positioned, and wherein the second membrane is a porous membrane that allows for select fluid and nutrients to pass to the cell layer, and wherein the cells of the pre-positioned cell layer are adapted to respond to physiological changes in the bodily fluid by emitting fluorescence; and
   (ii) an electronic component, wherein the electronic component comprises a light source for shining light onto the cell layer, thereby causing certain cells within the cell layer to emit fluorescence, wherein the emitted fluorescence, associated with the physiological changes, is an indication of blood pressure, ECG, heart rate, body temperature, gene and protein changes, local cellular changes that reflect systemic disease or change in health status, or combinations thereof; and
   a reader for detecting and/or decoding the emitted fluorescence from the cell layer to monitor physiological changes in the patient.

2. The device of claim 1, wherein the device is capable of substantially continuous monitoring.

3. The device of claim 1, wherein the housing is secured to the patient's body with a removable element.

4. The device of claim 3, wherein the removable element is an adhesive tape.

5. The device of claim 1, wherein the first membrane is made from glass.

6. The device of claim 1, wherein the chamber further comprises a microfluid pump for pumping fresh fluid over the cells.

7. The device of claim 1, wherein the chamber further comprises a waste fluid chamber.

8. The device of claim 7, wherein the waste fluid chamber receives and stores the fluid after it has passed over the cells.

9. The device of claim 1, wherein the device is capable of engaging in a two-way communication through transmission of one or more signals with a second device.

10. The device of claim 1, wherein the device further comprises a temperature sensor for monitoring temperature changes in the cells.

11. The device of claim 10, wherein the device further comprises a temperature controller for adjusting the temperature to a desired parameter.

12. A system for monitoring physiological changes in a patient, comprising:
    a wearable first device for use in monitoring physiological changes in the patient, comprising:
    a housing adapted to being secured to a patient's body, the housing comprising a needle which can be inserted into the patient subcutaneously or intravenously, and which is configured for fluid contact with a bodily fluid under a skin surface;
    a chamber situated within the housing, the chamber comprising:
    (i) a biological component, with a first membrane and a second membrane on either side of the biologic component, the biological component having a cell layer comprising cells, wherein the first membrane is a non-porous membrane on which the cell layer is pre-positioned, and wherein the second membrane is a porous membrane that allows for select fluid and nutrients to pass to the cell layer, and wherein the cells of the pre-positioned cell layer are adapted to respond to physiological changes in the bodily fluid by emitting fluorescence; and
    ii) an electronic component, wherein the electronic component comprises a light source for shining light onto the cell layer, thereby causing certain cells within the cell layer to emit fluorescence, wherein the emitted fluorescence, associated with the physiological changes, is an indication of the patient's blood pressure, ECG, heart rate, body temperature, gene and protein changes, local cellular changes that reflect systemic disease or change in health status, or combinations thereof; and
    a reader for detecting and/or decoding the emitted fluorescence from the cell layer to monitor physiological changes in the patient and for transmitting a signal to an external receiver, wherein the external receiver detects and decodes the signal, and in response, subsequently triggers an adjustment in drug delivery from a second device implanted within the patient's body, wherein the second device is capable of drug delivery.

13. A method of treating a patient, the method comprising:
    attaching a wearable first device for use in monitoring physiological changes to a patient, comprising:
    a housing adapted to being secured to a patient's body, the housing comprising a needle configured for fluid contact with a bodily fluid under a skin surface;
    a chamber situated within the housing, the chamber comprising a biological component having a cell layer and configured to monitor physiological changes in the bodily fluid and to generate one or more signals associated with the physiological changes, wherein the cell layer comprises cells pre-positioned on or in the wearable first device and wherein the pre-positioned cells are adapted to respond to a physiological signal from the patient by emitting fluorescence; and an electronic component, wherein the electronic component comprises a light source for shining light onto the cell layer, thereby causing certain cells within the cell layer to emit fluorescence, wherein the emitted fluorescence is an indication of the patient's blood pressure, ECG, heart rate, body temperature, gene and protein changes, local cellular changes that reflect systemic disease or change in health status, or combinations thereof; and a reader for detecting and/or decoding the emitted fluorescence from the cell layer to monitor physiological changes in the patient;

providing a second device spaced apart from the first device, wherein the second device is implanted into the patient's body and is capable of drug delivery, wherein the first device and second device capable of engaging in a two-way communication through transmission of signals through at least a portion of the patient's body between the first device and the second device;

detecting and/or decoding the one or more signals to monitor physiological changes in the patient;

reviewing and/or analyzing the one or more signals; and treating the patient based on the review and/or analysis of the one or more signals and initiating an adjustment in drug delivery from the second device.

\* \* \* \* \*